United States Patent
Wu et al.

[11] Patent Number: 6,121,317
[45] Date of Patent: Sep. 19, 2000

[54] GIBBERELLINS (INCLUDING GIBBERELLINS $A_3$ AND $A_7$) USED IN ULCER OR WOUND HEALING

[75] Inventors: Minne Wu; David Shine Wu, both of Mount Waverley, Australia

[73] Assignee: Australian Biomedical Company Pty. Ltd., Victoria, Australia

[21] Appl. No.: 09/188,593

[22] Filed: Nov. 9, 1998

Related U.S. Application Data

[63] Continuation-in-part of application No. 08/860,090, filed as application No. PCT/AU96/00003, Jan. 5, 1996, abandoned.

[30] Foreign Application Priority Data

| Jan. 6, 1995 | [AU] | Australia | .............. | PN0420 |
| Nov. 24, 1995 | [AU] | Australia | .............. | PN6777 |
| Dec. 5, 1995 | [AU] | Australia | .............. | PN6977 |

[51] Int. Cl.$^7$ .............. A61K 31/215; C07C 229/00; C07C 69/74
[52] U.S. Cl. .............. 514/530; 514/539; 560/35; 560/116; 560/117
[58] Field of Search .............. 514/530, 539; 560/116, 117, 35

[56] References Cited

U.S. PATENT DOCUMENTS

| 4,424,232 | 1/1984 | Parkinson | .............. | 424/279 |
| 5,487,899 | 1/1996 | Davis | .............. | 424/443 |
| 5,580,857 | 12/1996 | Oden | .............. | 514/25 |

FOREIGN PATENT DOCUMENTS

| 0079074 | 5/1983 | European Pat. Off. . |
| 282951 | 9/1988 | European Pat. Off. . |
| 2597339 | 10/1987 | France . |
| 8401710 | 5/1984 | WIPO . |
| 9426240 | 11/1994 | WIPO . |

OTHER PUBLICATIONS

Milman, N., et al., "Lysine Prophylaxis in Recurrent Herpes Simplex Labialis: A Double–Blind, Controlled Crossover Study." Acta Derm Venereal (Stockh) (1980) 60 (1) 85–7.
Milman, N., et al. "Lysine Prophylaxis in Recurrent Labial Herpes Simplex." Ugeskr Laeger, May 5, 1980: 142 (19): 1202–3 (Eng. Abstr.).
Milman, N., et al. "Lysine Therapy of Recurrent Herpes Simplex Labialis." Ugeskr Laeger (Oct. 22, 1979) 141 (43): 2960–2 (Eng. Abstr.).
Spadoni, R., et al. "Lysine P–isobutyl–phenylpropinate in Articular and Extra–articular Osteoarthritis." Clin Ter. (Apr. 15, 1979) 89 (1) 75–86 (Eng. Abstr.).
Furber, M., et al. "New Synthetic Pathways from Gibberellins to Antheridiogens Isolated from the Fern Genus *Anemia*." Journal of Organic Chemistry, vol. 55, No. 15 (Jul. 1990) pp. 4860–4870.
Berkow, et al. "The Merck Manual." 16th Edition (1992) pp. 2401–2406.

*Primary Examiner*—Mukund J. Shah
*Assistant Examiner*—Tamthom N. Truong
*Attorney, Agent, or Firm*—Ladas & Parry

[57] ABSTRACT

Compounds of formula (1), (Gibberellins), and their pharmaceutically acceptable derivatives to promote ulcer-healing, healing of surgical wounds or open fractures and treatment of bronchitis or thrombophlebitis in animals including humans or cultivation of skin cell lines in vitro

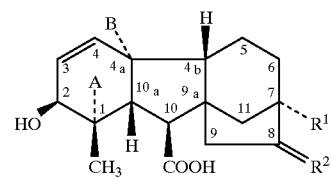

(1)

wherein A is COOR, where R is hydrogen, unsubstituted or substituted $C_{1-20}$ alkyl, allyl, aryl, arylalkyl, amidine, $NR^4R^5$ or an unsaturated or saturated ring containing one or more hetero-atoms selected from the group consisting of nitrogen, oxygen and sulfur; $R^4$ and $R^5$ may or may not be the same, are hydrogen, or $C_{1-20}$ alkyl, allyl, aryl, arylalkyl or an unsaturated or saturated ring containing one or more hetero-atoms selected from the group consisting of nitrogen and sulfur; B is hydrogen, hydroxyl, mercaptan, or halogen, or A and B together form a —CO—O— linkage; $R^1$ is hydrogen, hydroxyl, mercaptan, halogen, amino, azido, $NR^4R^5$, unsubstituted or substituted $C_{1-20}$ alkyl, allyl, aryl, arylalkyl, and $R^2$ is methylene, or a divalent hetero-atom.

22 Claims, 4 Drawing Sheets

GIBBERELLINS (INCLUDING GIBBERELLINS A₃ AND A₇) USED IN ULCER OR WOUND HEALING

This application is a continuation-in-part of U.S. patent application Ser. No. 08/860,090 filed on Jul. 2, 1997 now abandoned which is a national phase entry of PCT application PCT/AU96/00003 filed on Jan. 5, 1996.

This invention relates to a novel application of Gibberellins in veterinary and human medicines. In particular the invention concerns Gibberellins' pharmaceutical formulations and their use as ulcer-healing and wound-healing promoters, and their related conditions.

Gibberellins are a series of naturally occurring compounds, which are known as plant growth regulators with wide application in the plant-kingdom. [1] They have also been isolated from metabolites of some microorganisms, such as Gibberella fuzikuroi. [2] Gibberellins, especially Gibberellic Acid (Gibberellin A₃), have been used extensively in agriculture to increase the growth of some fruits (strawberries and grapes) and vegetables (tomatoes, cabbages and cauliflowers), also as food additive in the malting of barley. [3].

[1]. J. MacMillian, et al. "Isolation and Structure of Gibberellin From Higher Plants". Adv. Chem. Ser 28, 18~24, (1961).

[2].
  (a). P. J. Curtis et al. Chem. & Ind. (London) 1066, (1954).
  (b). B. E. Cross, J. Chem. Soc. 4670, (1954).
  (c). P. W. Brian et al, U.S. Pat. No. 2,842,051.
  (d). C. T. Calam et al, U.S. Pat. No. 2,950,288.
  (e). A. J. Birch et al, U.S. Pat. No. 2,977,285.

[3].
  (a). M. Devlin, Plant Physiology, New York, Reinhold, (1966).
  (b). P. W. Brian et al, Plant Physiol, 5,669 (1955).
  (c). A. K. Mehta et al, J. Hostic Sci 4, 167 (1975).
  (d). R. J. Weavor, Adv. Chem. Ser 28, 89 (1961).
  (e). F. G. Gustafson, Plant Physical 35, 521 (1960).
  (f). Fed. Reg. 25, 2162 (1960).

In U.S. Pat. No. 5,580,857 (Oden), reference is made to the use of Gibberellins for the treatment of prostatitis, an inflammatory condition of the prostate. Oden concluded that Gibberellins had a glucocorticoid- or steroid-like action, which resulted in an antiphlogistic (anti-inflammatory) effect. It was also postulated that Gibberellins may be used to treat psoriasis, (a form of dermatosis), burns and radiation burns, and for the stimulation of wound healing.

Steroids are well known in the treatment of inflammatory dermatoses and related inflammatory conditions. However, it is equally well known that steroids are implicated as a cause of ulcers, and in the impairment of wound healing, and Oden makes no reference to treatment of ulcers or to treatment of surgical wounds using Gibberellins. Despite the teaching of Oden, which suggests that, whilst perhaps useful for some wounds, Gibberellins would not be suitable for wounds where cortico-steroids would be contra-indicated, it has now been found that Gibberellins, especially Gibberellic acid (Gibberellin A₃) and/or a mixture of Gibberellins A₃ and A₇ are promoters of ulcer-healing, surgical wound-healing and cultivation of skin cell lines, which would play a significant role in veterinary and human medicines. This invention therefore provides a series of novel applications of compounds of formula (1) in both veterinary and human medicines,

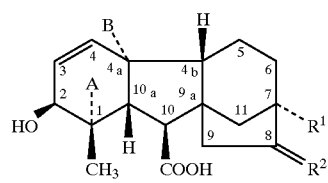

(1)

wherein

A is COOR, where R is hydrogen, unsubstituted or substituted (e.g. halogenated) $C_{1-20}$ alkyl, (e.g. methyl, ethyl), allyl, aryl, (e.g. phenyl), arylalkyl, amidine, $NR^4R^5$ or an unsaturated or saturated ring containing one or more hetero-atoms selected from the group consisting of nitrogen, oxygen or sulphur. $R^4$ and $R^5$ which may or may not be the same, are hydrogen, or $C_{1-20}$ alkyl (e.g. methyl, ethyl), allyl, aryl, arylalkyl or an unsaturated or saturated ring containing one or more hetero-atoms selected from the group consisting of nitrogen, oxygen, sulphur;

B is hydrogen, hydroxyl, mercaptan, halogen (e.g. Cl, F), or A and B together form a —CO—O— linkage, $R^1$ is hydrogen, hydroxyl, mercaptan, halogen, (e.g. F, Cl), amino, azido, $NR^4R^5$, unsubstituted or substituted (e.g. halogenated) $C_{1-20}$ alkyl, allyl, aryl, arylalkyl, and $R^2$ is methylene, or divalent hetero-atoms (e.g. oxygen, sulphur).

In the case of Gibberellin A₃, A—B is ———CO—O———, $R^1$ is hydroxyl, $R^2$ is methylene.

Pharmaceutically acceptable salts of the compounds of formula (1) include alkali metal (e.g. sodium, potassium), alkaline earth metal (e.g. calcium, magnesium), ammonium, and organic bases such as $NR^6R^7R^8R^9$ (where $R^6, R^7, R^8, R^9$ which may be the same or not the same, are $C_{1-20}$ alkyl or alkanol, aryl), procaine, lidocaine and the like.

Pharmaceutically acceptable compositions of the compounds of formula (1) may also be formed by combining them with one or more other active ingredients, for example, urea, antibiotics (e.g. streptomycin, getamycin, kanamycin, neomycin, penicillin, cephalosporin, rifamycin), antiseptic agents (e.g. cetylpyridinium chloride, benzoic acid salt), Vitamins (e.g. Vitamin E), sucrose, β-1,3-glucan, surfactants, cream-bases, herbs (e.g. panax pseudoginseng).

References hereinafter to the compounds of formula (1) include the compounds of formula (1), and the pharmaceutically acceptable derivatives thereof.

The compounds of formula (1) possess activity as promoters of ulcer-healing, wound-healing and cultivation of skin cell lines, possibly by stimulating cell division, hastening circulation and promoting repairing. There is thus provided in a further aspect of the invention the compounds of formula (1) for use as an active therapeutic agent, in particular as an ulcer-healing and wound-healing agent in the treatment of ulcers, wounds and related conditions, for example, in the treatment of surgical wounds, open fractures, bronchitis, thrombophlebitis, leg ulcer, peptic ulcer, aphthous ulcer or decubitus ulcers. There is also provided in a further aspect of the invention the compounds of formula (1) for use as an active agent in promoting the cultivation of skin cell lines for plastic surgery.

In a further or alternative aspect there is provided a method for the treatment of ulcers, wounds and related conditions in animals including humans comprising administering an effective amount of the compounds of formula (1).

There is also provided in a further or alternative aspect use of the compounds of formula (1) for the manufacture of a medicament for the treatment of wounds or ulcers, or related conditions.

The amount of the compounds of formula (1) required for use in treatment will vary with the route of administration, the nature of the condition being treated and the age and condition of the animal (including human patients) and will ultimately be at the discretion of the attendant veterinarian or surgeon.

In general a suitable dose will be in the range of from about 0.1 µg to 50 mg/kg of body weight per day, preferably in the range of 0.1 µg to 2,000 µg/kg/day.

Treatment is preferably commenced after or at the time the ulcer or wound occurs and continues until the ulcer or wound is healed. Suitably treatment is given 1~4 times daily and continued for 3~30 days. Alternatively, in some cases like open fracture or internal surgical wounds, a single treatment may be administered on the spot.

The desired dose may be presented in a single dose or as divided doses administered at appropriate intervals, for example as two, three, four or more sub-doses per day.

The compounds of formula (1) are conveniently administered in unit dosage form for example containing 0.1 to 50 mg of active ingredient per unit dosage form.

While it is possible that, for use in therapy, the compounds of formula (1) may be administered as the raw chemical it is preferable to present the active ingredient as a pharmaceutical formulation.

The invention thus further provides a pharmaceutical formulation including the compounds of formula (1) or a pharmaceutically acceptable derivative thereof together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, intradermal, sub-cutaneous and intravenous) administration or in a form suitable for administration to the gastrointestinal tract, or in a form suitable for administration to the respiratory tract (including the nasal passages) for example by inhalation or insufflation or for intradermal or sub-cutaneous implantation or for transdermal patch. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation. Pharmaceutical formulations suitable for oral administration may be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds of formula (1) may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis the compounds of formula (1) may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening, or colouring agents.

For topical administration in the mouth, the compounds of formula (1) may be formulated as lozenges comprising active ingredient in a flavored base, usually sucrose and acacia or tragacanth; pastilles comprising the active ingredient in an inert base such as gelatine and glycerin or sucrose and acacia; and mouthwashes comprising the active ingredient in a suitable liquid carrier.

For vaginal administration the formulations may be presented as pessaries, tampons, creams, gels, pastes, foams or sprays containing in addition to the active ingredient such carriers as are known in the art to be appropriate.

For rectal administration, unit dose suppositories wherein the carrier is a solid are preferred. Suitable carriers include cocoa butter and other materials commonly used in the art, and the suppositories may be conveniently formed by admixture of the active compound with the softened or melted carrier(s) followed by chilling and shaping in moulds.

For administration to the respiratory tract (including intranasal administration) compounds of formula (1) may be administered by any of the methods and formulations employed in the art for administration to the respiratory tract.

Thus in general the compounds of formula (1) may be administered in the form of a solution or a suspension or as a dry powder.

Solutions and suspensions will preferably be aqueous for example prepared from water alone (for example sterile or pyrogen-free water) or water and a physiologically acceptable co-solvent (for example ethanol, propylene glycol, polyethylene glycols such as PEG 400).

Such solutions or suspensions may additionally contain other excipients for example preservatives (such as benzalkonium chloride), solubilising agents/surfactants such as polysorbates (e.g. Tween 80, Span 80, benzalkonium chloride), buffers, isotonicity-adjusting agents (for example sodium chloride), absorption enhancers and viscosity enhancers. Suspensions may additionally contain suspending agents (for example microcrystalline cellulose, carboxymethyl cellulose sodium).

Solutions or suspensions are applied directly to the nasal cavity by conventional means, for example with a dropper, pipette or spray. The formulations may be provided in single or multidose form. In the latter case a means of dose metering is desirably provided. In the case of a dropper or pipette this may be achieved by the patient administering an appropriate, predetermined volume of the solution or suspension. In the case of a spray this may be achieved for example by means of a metering atomizing spray pump.

An aerosol formulation may also be used for the respiratory tract administration, in which the compounds of formula (1) are provided in a pressurized pack with a suitable propellant such as a chlorofluorocarbon (CFC) for example dichlorodifluoromethane, trichlorofluoromethane or dichlorotetrafluoroethane, carbon dioxide or other suitable gas. The aerosol may conveniently also contain a surfactant such as lecithin. The dose of drug may be controlled by provision of a metered valve.

Alternatively the compounds of formula (1) may be provided in the form of a dry powder, for example a powder mix of the compound in a suitable powder base such as lactose, starch, starch derivatives such as hydroxypropylmethyl cellulose and polyvinylpyrrolidine (PVP). Conveniently the powder carrier will form a gel in the nasal cavity. The powder composition may be presented in unit dose form for example in capsules or cartridges of e.g. gelatine or blister packs from which the powder may be administered by means of an inhaler.

In formulations intended for administration to the respiratory tract, including intranasal formulations, the compound will generally have a small particle size for example of the order of 5 microns or less. Such a particle size may be obtained by means known in the art, for example by micronisation.

For administration to the gastrointestinal ulcer such as peptic ulcer, the compounds of formula (1) or a pharmaceutically acceptable derivative may be administered by any of the methods and formulations employed in the art for administration to the gastrointestinal tract.

When desired, formulations adapted to give sustained release of the active ingredient may be employed.

The compounds of formula (1) may also be used in combination with other therapeutic agents, for example anti-infective agents, such as antibiotics or wound healing agents such as 1,3-β-glucan. The invention thus provides in a further aspect a combination comprising the compounds of formula (1) or a pharmaceutically acceptable derivative thereof together with another therapeutically active agent.

The combinations mentioned above may conveniently be presented for use in the form of a pharmaceutical formulation and thus such formulations comprising a combination as defined above together with a pharmaceutically acceptable carrier therefore comprise a further aspect of the invention.

The individual components of such combinations may be administered either sequentially or simultaneously in separate or combined pharmaceutical formulations.

When the compounds of formula (1) are used with a second therapeutic agent active in wound-healing, the dose of each compound may either be the same as or differ from that employed when each compound is used alone. Appropriate doses will be readily appreciated by those skilled in the art.

The compounds of formula (1) and their pharmaceutically acceptable derivatives may be prepared by any methods known in the art for the preparation of compounds of analogous structure.

In addition to the findings described above, we have also discovered that the compounds of formula (1) promote hair growth in mammals including humans. This is a logical extension of what is believed to be their mode of action, which involves stimulating cell division.

The present invention is further described by the following examples, which are for illustrative purposes only and should not be construed as a limitation of the invention.

METHODS

Figure 1:
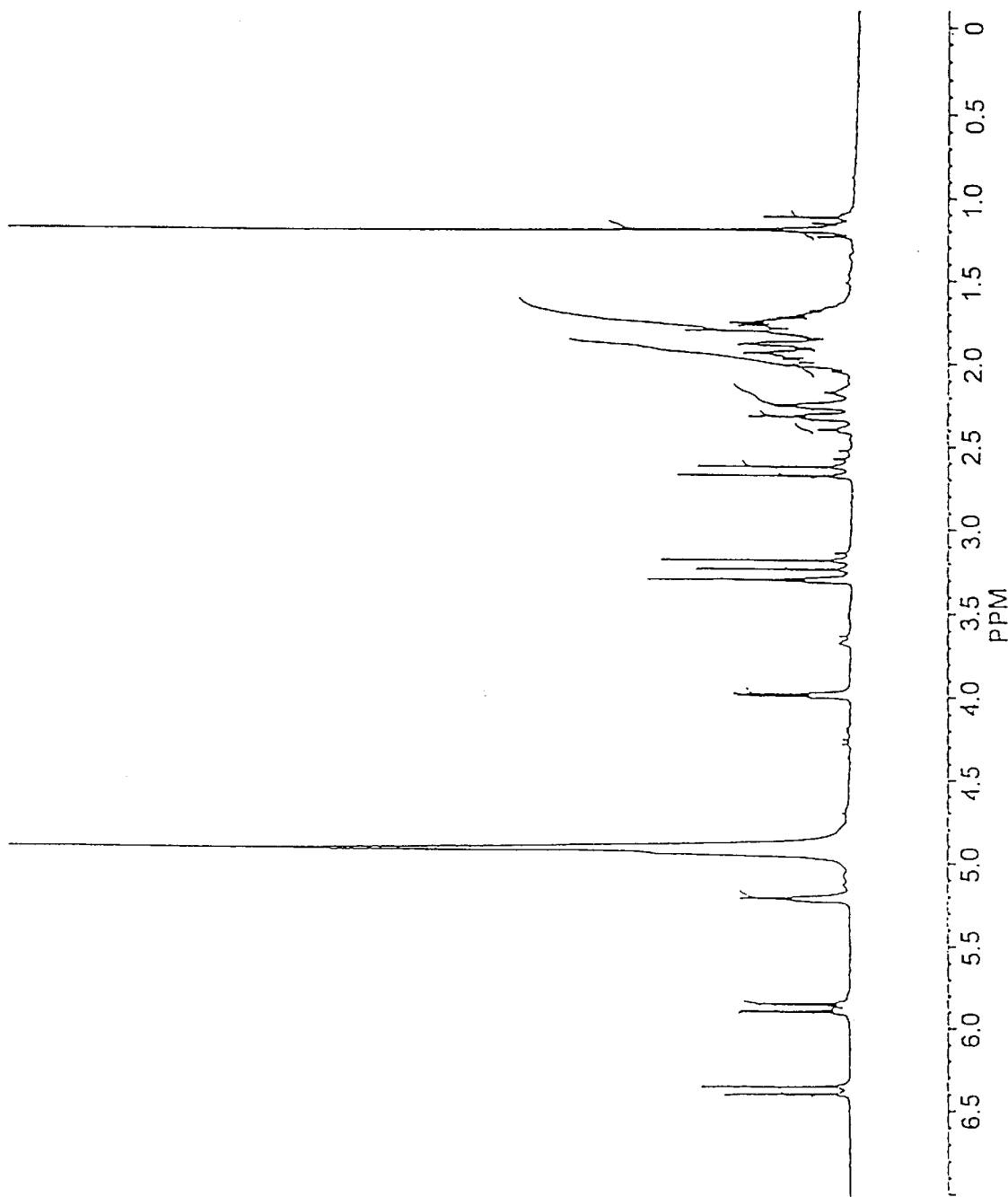
FIG. 1 shows the $^1$H-nmr spectrum for the free acids of compounds of Formula 1.
Figure 2:
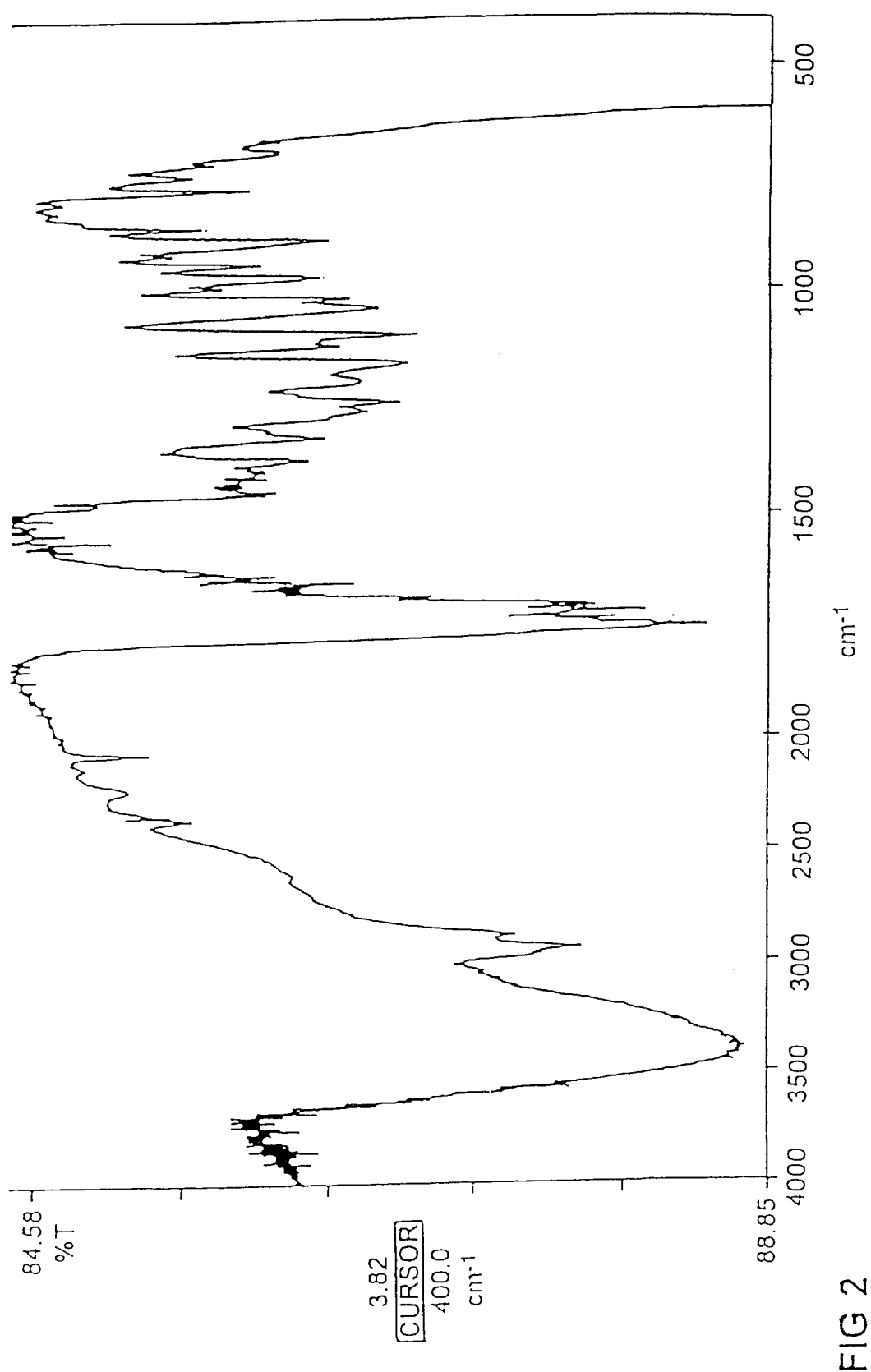
FIG. 2 shows the IR spectrum for the free acids of compounds of Formula 1.
Figure 3:
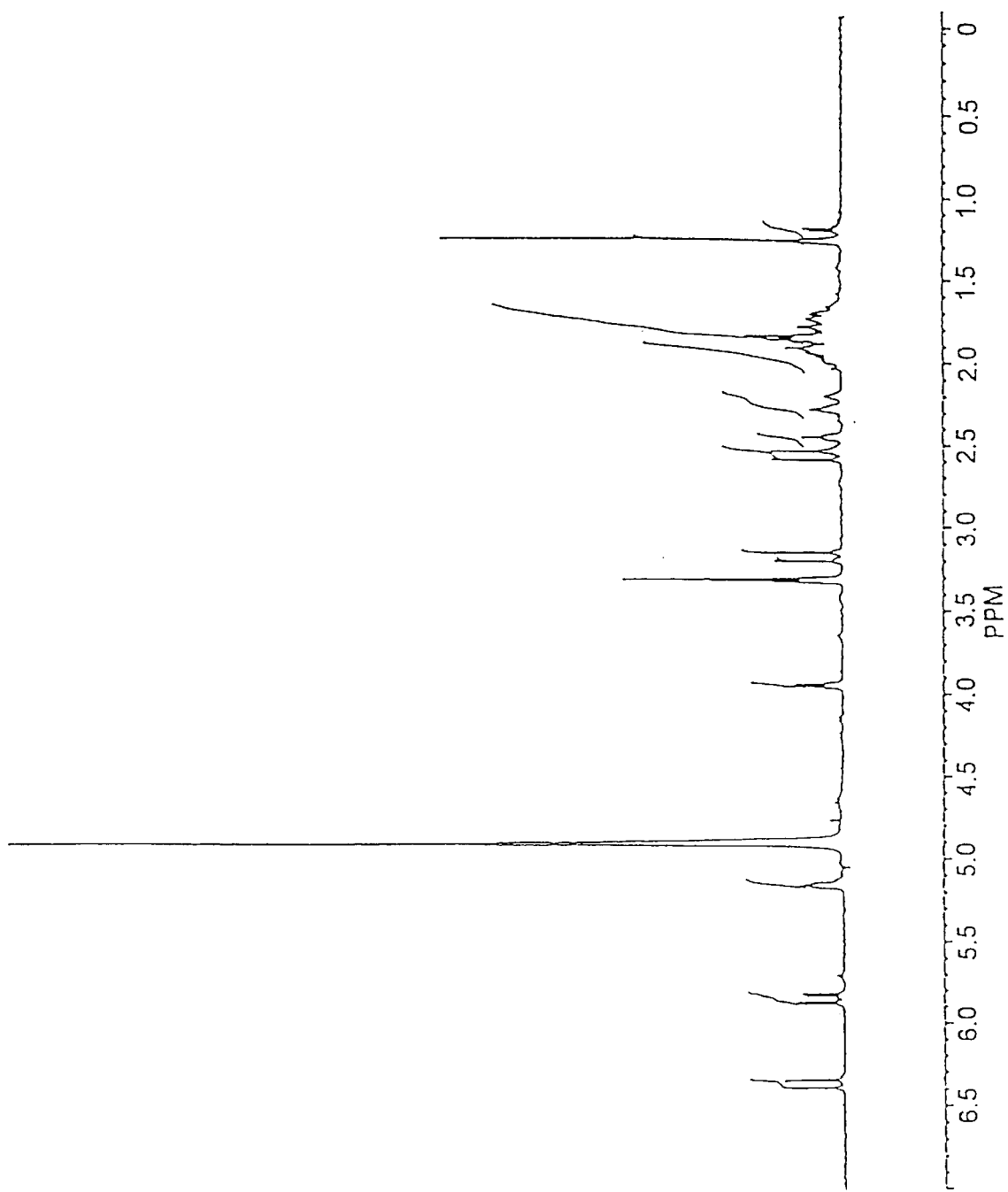
FIG. 3 shows the $^1$H-nmr spectrum for the sodium salts of compounds of Formula 1.
Figure 4:
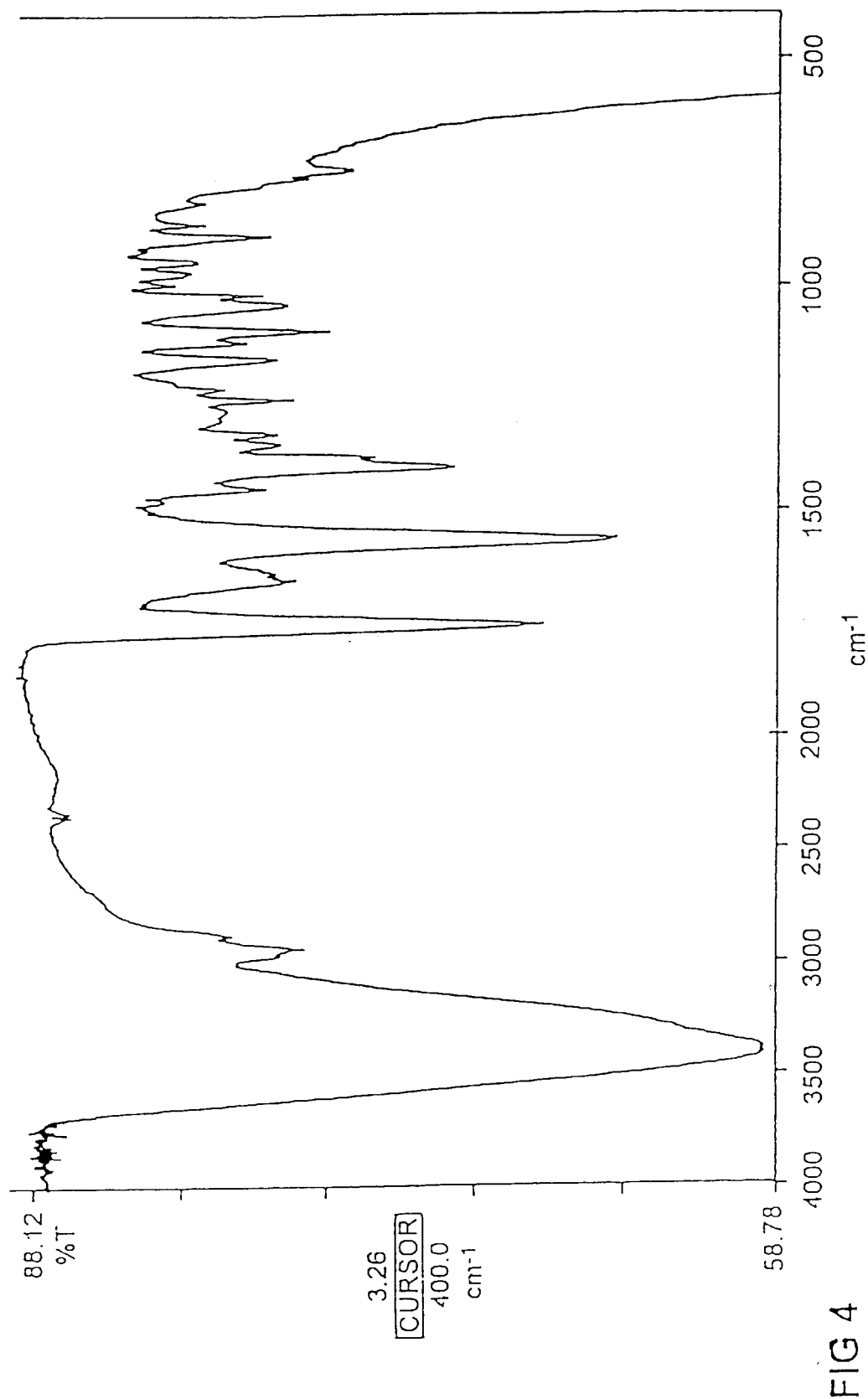
FIG. 4 shows the IR spectrum for the sodium salts of compounds of Formula 1.

Material: The compounds of formula (1) used in the following experiments were free acid (its 1H-nmr shown in FIG. 1, and IR spectrum shown in FIG. 2) and/or sodium salt (its 1H-nmr shown in FIG. 3, and IR spectrum shown in FIG. 4).

Statistical analysis: All statistical analysis for the following experimental results were performed two-tailed at a significance level of P=0.05.

EXAMPLE 1

Topical use of Compounds of Formula (1)

The compounds of formula (1) may be used topically as their aqueous solution or in oil base as ointment form at a concentration of 0.1 to 20,000 μg per milli-liter, preferably at 0.1 to 100 μg/ml.

EXAMPLE 2

Surface-wound Healing

Gibberellin A3 (1 mg) was dissolved in ethanol (1 ml), then diluted with distilled water (99 ml) to make a solution at a concentration of 10 μg/ml. This solution was directly applied on wounds (cuts, at about 2 cm in length, and about 1 mm in depth) of pigs by spreading the solution twice a day until the wounds healed. The control group of the animals was treated with 1% ethanol aqueous solution. The average rates of wound healing increased by one third in Gibberellin-administered group compared to the controls in this double-blind experiment.

EXAMPLE 3

Surface-wound Healing

Gibberellin $A_3$ sodium salt was used in aqueous solution (20 μg/ml) instead of Gibberellin $A_3$ free acid mentioned in example 2. The similar results as example 2 were obtained.

EXAMPLE 4

Surface-wound Healing

A solution containing 10 μg/ml Gibberellin $A_3$ sodium salt and 500 μg/ml urea was used. The similar animal experiment mentioned in Example 2 was conducted. About 25% of increase of wound healing rates in Gibberellin $A_3$ and urea administered group compared to the control group using only urea solution was observed in this double-blind experiment.

EXAMPLE 5

Chronic Ulceration of Leg Caused by Varicose Vein

Gibberellin $A_3$ or a mixture of $A_3$ and $A_7$ (2 mg) was dissolved in ethanol (1 ml), then diluted with distilled water (99 ml). This resulting solution was spread on the surface of the ulcer twice a day for a period of five days to three weeks. An 85% efficacy was observed.

EXAMPLE 6

Some Double-blind Trials for Gibberellin $A_3$ Sodium Salt

| Case of Treatment | Administration | | | Efficacy |
|---|---|---|---|---|
| | Route | Dosage or Concentration | Duration | |
| Thrombophlebitis | topical | 20–50 μg/ml, 2–4 times daily | 5 days to 4 weeks | 85% |
| Open fracture | topical on the spot of wound | 200–500 μg/ul*[1], once only | | 75% (increased recovery rate by 10%) |
| Bronchitis | aerosol for respiratory tract | 5–10 μg/ml*[2], 2–4 times daily | 3 days to 2 weeks | 80% |
| Peptic ulcer | oral | 5 mg*[3], twice daily | 2 to 4 weeks | 85% |
| Aphthous ulcer | topical (gargle) | 50~1000 μg/ml*[4], 2~3 times daily | 3 days to 2 weeks | 80% |
| Decubitus | topical | 20~50 μg/ml*[5], 2–times daily | 5 days to 3 weeks | 75% |

*[1]Combination with antibiotics such as neomycin sulfate.
*[2]In some cases patients were also treated with antibiotics such as amoxicillin.
*[3]Combination with antibiotics such as streptomycin sulfate (0.5g)/ampicillin (0.5g), and bismuth citrate, or milk-starch, and/or ranitidine.
*[4]In some cases, combination with cetylpyridinium chloride as anticeptic agent.
*[5]Combination with antibiotics such as Midecamycin/Doxycycline.

What is claimed is:

1. A method of treatment comprising adhibiting compounds of formula (1), (Gibberellins), and their pharmaceutically acceptable derivatives in the absence of added lysine as an active agent, to promote ulcer-healing, healing of open fractures and treatment of bronchitis or thrombophlebitis in animals including humans or cultivation of skin cell lines in vitro.

(1)

wherein
A is COOR, where R is hydrogen, unsubstituted or substituted $C_{1-20}$ alkyl, allyl, aryl, arylalkyl, amidine, $NR^4R^5$ or an unsaturated or saturated ring containing one or more hetero-atoms selected from the group consisting of nitrogen, oxygen and sulfur; $R^4$ and $R^5$ may be the same or different, and represent hydrogen, or $C_{1-20}$ alkyl, allyl, aryl, arylalkyl or an unsaturated or saturated ring containing one or more hetero-atoms selected from the group consisting of nitrogen, oxygen and sulfur;

B is hydrogen, hydroxyl, mercaptan, or halogen, or A and B together form a —CO—O— linkage, $R^1$ is hydrogen, hydroxyl, mercaptan, halogen, amino, azido, $NR^4R^5$, unsubstituted or substituted $C_{1-20}$ alkyl, allyl, aryl, or arylalkyl, and $R^2$ is methylene, or a divalent hetero-atom.

2. The method of claim 1, wherein the Gibberellins are Gibberellin $A_3$ so that A—B is —CO—O—, $R^1$ is hydroxyl and $R^2$ is methylene.

3. The method of claim 1, wherein the Gibberellins are a mixture of Gibberellin $A_3$ and Gibberellin $A_7$.

4. The method of claim 1, wherein the pharmaceutically acceptable derivatives are salts, including alkali metal salts, alkaline earth metal salts, and salts of ammonium, organic bases, procaine, or lidocaine.

5. The method of claim 4, wherein the organic base is $NR^6R^7R^8R^9$, where $R^6$, $R^7$, $R^8$ and $R^9$ may be the same or different and are $C_{1-20}$ alkyl, alkanol or aryl.

6. A method of promoting ulcer-healing, comprising administering an effective amount of a compound of formula (1) (Gibberellins)

(1)

wherein
A is COOR, where R is hydrogen, unsubstituted or substituted $C_{1-20}$ alkyl, allyl, aryl, arylalkyl, amidine, $NR^4R^5$ or an unsaturated or saturated ring containing one or more hetero-atoms selected from the group consisting of nitrogen, oxygen and sulfur; $R^4$ and $R^5$ may or may not be the same, are hydrogen, or $C_{1-20}$ alkyl, allyl, aryl, arylalkyl or an unsaturated or saturated ring containing one or more hetero-atoms selected from the group consisting of nitrogen, oxygen and sulphur;

B is hydrogen, hydroxyl, mercaptan, or halogen, or A and B together form a —CO—O— linkage, $R^1$ is hydrogen, hydroxyl, mercaptan, halogen, amino, azido, $NR^4R^5$, unsubstituted or substituted $C_{1-20}$ alkyl, allyl, aryl, or arylalkyl, and $R^2$ is methylene, or a divalent hetero-atom, to a patient in need thereof.

7. A method according to claim 6, wherein the Gibberellins are Gibberellin $A_3$.

8. A method according to claim 6, wherein the Gibberellins are a mixture of Gibberellin $A_3$ and Gibberellin $A_7$.

9. The method of claim 6, when used in the treatment of leg ulcer, peptic ulcer, aphthous ulcer or decubitus ulcer.

10. A method of treating bronchitis or thrombophlebitis comprising administering an effective amount of a compound of formula (1) (Gibberellins)

(1)

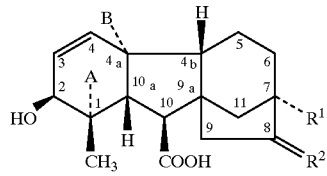

wherein

A is COOR, where R is hydrogen, unsubstituted or substituted $C_{1-20}$ alkyl, allyl, aryl, arylalkyl, amidine, $NR^4R^5$ or an unsaturated or saturated ring containing one or more hetero-atoms selected from the group consisting of nitrogen, oxygen and sulfur; $R^4$ and $R^5$ may or may not be the same, are hydrogen, or $C_{1-20}$ alkyl, allyl, aryl, arylalkyl or an unsaturated or saturated ring containing one or more hetero-atoms selected from the group consisting of nitrogen, oxygen and sulphur;

B is hydrogen, hydroxyl, mercaptan, or halogen, or A and B together form a —CO—O— linkage, $R^1$ is hydrogen, hydroxyl, mercaptan, halogen, amino, azido, $NR^4R^5$, unsubstituted or substituted $C_{1-20}$ alkyl, allyl, aryl, or arylalkyl, and $R^2$ is methylene, or a divalent hetero-atom, to a patient in need thereof.

11. A method according to claim 10, wherein the Gibberellins are Gibberellin $A_3$.

12. A method according to claim 11, wherein the Gibberellins are a mixture of Gibberellin $A_3$ and Gibberellin $A_7$.

13. A method of promoting healing of open fractures comprising administering an effective amount of a compound of formula (1) (Gibberellin)

(1)

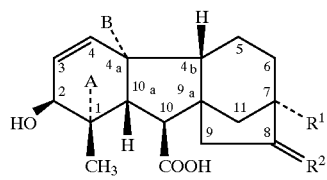

wherein

A is COOR, where R is hydrogen, unsubstituted or substituted $C_{1-20}$ alkyl, allyl, aryl, arylalkyl, amidine, $NR^4R^5$ or an unsaturated or saturated ring containing one or more hetero-atoms selected from the group consisting of nitrogen, oxygen and sulfur; $R^4$ and $R^5$ may or may not be the same, are hydrogen, or $C_{1-20}$ alkyl, allyl, aryl, arylalkyl or an unsaturated or saturated ring containing one or more hetero-atoms selected from the group consisting of nitrogen, oxygen and sulphur;

B is hydrogen, hydroxyl, mercaptan, or halogen, or A and B together form a —CO—O— linkage, $R^1$ is hydrogen, hydroxyl, mercaptan, halogen, amino, azido, $NR^4R^5$, unsubstituted or substituted $C_{1-20}$ alkyl, allyl, aryl, or arylalkyl, and $R^2$ is methylene, or a divalent hetero-atom, to a patient in need thereof.

14. A method according to claim 13, wherein the Gibberellins are Gibberellin $A_3$ and $A_7$.

15. A method according to claim 13, wherein the Gibberellins are a mixture of Gibberellins $A_3$ and Gibberellin $A_7$.

16. A method of promoting cultivation of skin cell lines in vitro including providing an effective amount of a compound of formula (1) (Gibberellin)

(1)

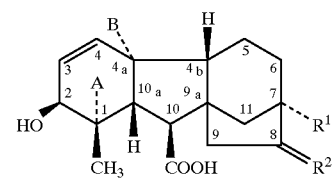

wherein

A is COOR, where R is hydrogen, unsubstituted or substituted $C_{1-20}$ alkyl, allyl, aryl, arylalkyl, amidine, $NR^4R^5$ or an unsaturated or saturated ring containing one or more hetero-atoms selected from the group consisting of nitrogen, oxygen and sulfur; $R^4$ and $R^5$ may or may not be the same, are hydrogen, or $C_{1-20}$ alkyl, allyl, aryl, arylalkyl or an unsaturated or saturated ring containing one or more hetero-atoms selected from the group consisting of nitrogen, oxygen and sulfur;

B is hydrogen, hydroxyl, mercaptan, or halogen, or A and B together form a —CO—O— linkage, $R^1$ is hydrogen, hydroxyl, mercaptan, halogen, amino, azido, $NR^4R^5$, unsubstituted or substituted $C_{1-20}$ alkyl, allyl, aryl, or arylalkyl, and $R^2$ is methylene, or a divalent hetero-atom, to a skin cell line culture.

17. A method according to claim 16, when used in the promotion of cultivation of skin cell lines for plastic surgery.

18. A method according to claim 16, wherein the Gibberellins are Gibberellin $A_3$ and $A_7$.

19. A method according to claim 16, wherein the Gibberellins are a mixture of Gibberellin $A_3$ and Gibberellin $A_7$.

20. A pharmaceutical composition comprising a compound of formula (1), as an active ingredient, (1)

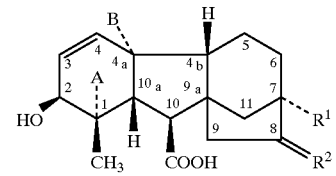

wherein

A is COOR, where R is hydrogen, unsubstituted or substituted $C_{1-20}$ alkyl, allyl, aryl, arylalkyl, amidine, $NR^4R^5$ or an unsaturated or saturated ring containing one or more hetero-atoms selected from the group consisting of nitrogen, oxygen and sulfur; $R^4$ and $R^5$ which may or may not be the same, are hydrogen, or $C_{1-20}$ alkyl, allyl, aryl, arylalkyl or an unsaturated or saturated ring containing one or more hetero-atoms selected from the group consisting of nitrogen, oxygen and sulfur;

B is hydrogen, hydroxyl, mercaptan, or halogen, or A and B together form a —CO—O— linkage, $R^1$ is hydrogen, hydroxyl, mercaptan, halogen, amino, azido, $NR^4R^5$, unsubstituted or substituted $C_{1-20}$ alkyl, allyl, aryl, and $R^2$ is methylene, or a divalent hetero-atoms;

a further active ingredient selected from urea, antibiotics, antiseptic agents, vitamins, β-1,3-glucan, medicinal herbs or mixtures thereof and a pharmaceutically acceptable carrier.

21. A pharmaceutical composition according to claim 20, wherein the carrier is selected from sucrose, acacia, tragicanth, gelatin, glycerin, cocoa butter, propylene glycol, polyethylene glycols, benzolkamium chloride, polysorbates, buffers, isotonicity-adjusting agents, absorption enhancers, viscosity enhancers, suspending agents, surfactants, lactose, starch or starch derivatives and mixtures thereof.

22. A method of manufacturing a composition according to claim 20, comprising combining a compound of formula (1)

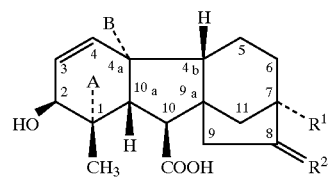

wherein

A is COOR, where R is hydrogen, unsubstituted or substituted $C_{1-20}$ alkyl, allyl, aryl, arylalkyl, amidine, $NR^4R^5$ or an unsaturated or saturated ring containing one or more hetero-atoms selected from the group consisting of nitrogen, oxygen and sulfur; $R^4$ and $R^5$ may or may not be the same, are hydrogen, or $C_{1-20}$ alkyl, allyl, aryl, arylalkyl or an unsaturated or saturated ring containing one or more hetero-atoms selected from the group consisting of nitrogen, oxygen and sulfur;

B is hydrogen, hydroxyl, mercaptan, or halogen, or A and B together form a —CO—O— linkage, $R^1$ is hydrogen, hydroxyl, mercaptan, halogen, amino, azido, $NR^4R^5$, unsubstituted or substituted $C_{1-20}$ alkyl, allyl, aryl, or arylalkyl, and $R^2$ is methylene, or a divalent hetero-atom; and a further active ingredient selected from urea, antibiotics, antiseptic agents, vitamins, β-1,3-glucan, medicinal herbs or mixtures thereof, with a pharmaceutically acceptable carrier.

* * * * *